US005430138A

United States Patent [19]

Urdea et al.

[11] Patent Number: 5,430,138

[45] Date of Patent: Jul. 4, 1995

[54] HYDROXYL-PROTECTING GROUPS ATTACHED TO CYTIDINE NUCLEOTIDE COMPOUNDS WHICH ARE ORTHOGONALLY REMOVABLE

[75] Inventors: Michael S. Urdea, Alamo; Thomas Horn, Berkeley, both of Calif.

[73] Assignee: Chiron Corporation, Emeryville, Calif.

[21] Appl. No.: 558,881

[22] Filed: Jul. 27, 1990

[51] Int. Cl.[6] .......... C07H 19/073

[52] U.S. Cl. .......... 536/26.8; 536/28.5; 536/28.51; 536/28.52

[58] Field of Search .......... 536/23, 24, 29, 28, 536/23.1, 24.3, 25.3, 25.31, 25.32, 26.8, 28.5, 28.51, 28.52

[56] References Cited

U.S. PATENT DOCUMENTS

| | | | |
|---|---|---|---|
| 4,837,311 | 6/1989 | Tam et al. | 536/22 |
| 4,843,122 | 6/1989 | Stavrianopoulos | 536/27 |
| 4,910,300 | 3/1990 | Urdea et al. | 536/26.8 |
| 5,043,325 | 8/1991 | Olsson et al. . | |
| 5,093,232 | 3/1992 | Urdea et al. | 435/6 |
| 5,118,802 | 6/1992 | Smith et al. | 536/27 |
| 5,367,066 | 11/1994 | Urdea et al. | 536/24.3 |

OTHER PUBLICATIONS

D. S. Kemp et al., *Tetrahedron Letters*, No. 12, pp. 1031–1034 (1977).

N. Balgobin et al., *Chemica Scripta* 20:198–200 (1982).

R. L. Blankespoor et al., *J. Org. Chem.* 49:4441–46 (1984).

Balgobin et al., Letter to Chemica Scripta, vol. 20, pp. 198–200, (1982).

Blankespoor et al., J. of Org. Chem, vol. 49, pp. 4441–4446, (1984).

*Primary Examiner*—Douglas W. Robinson
*Assistant Examiner*—James O. Wilson
*Attorney, Agent, or Firm*—Reed & Robins; Kenneth M. Goldman; Robert P. Blackburn

[57] ABSTRACT

Hydroxyl-protecting groups orthogonally removable by reduction with a liquid reducing agent are disclosed. The novel hydroxyl-protecting groups are particularly useful in the chemical synthesis of linear and branched oligonucleotide structures, as they are readily removed from the protected molecule with mild reagents such as dithionite. Examples of such hydroxyl-protecting groups include the 2-methylene-9,10-anthraquinone (Maq) carbonate ester and the p-nitrobenzyl carbonate ester.

7 Claims, No Drawings

HYDROXYL-PROTECTING GROUPS ATTACHED TO CYTIDINE NUCLEOTIDE COMPOUNDS WHICH ARE ORTHOGONALLY REMOVABLE

TECHNICAL FIELD

This invention relates generally to hydroxyl-protecting groups and more particularly relates to hydroxyl-protecting groups which are orthogonally removable by reduction with liquid reducing agents and which are especially useful in the chemical synthesis of oligonucleotides.

Background

With the advent of hybrid DNA technology and the explosion in the ability to isolate, purify and assay a wide variety of natural products, there is an increasing need for rapid and efficient methods of preparing and purifying oligomers of nucleic acids and amino acids.

With nucleic acids, it is typically necessary to synthesize sequences for use as linkers, adapters, synthetic genes, and synthetic regulatory sequences, as well as for use as probes, primers, and the like. Many procedures have been developed for producing oligomers of nucleotides, or "oligonucleotides". These procedures for the most part rely on initial attachment of a first nucleotide to a solid support, followed by the sequential addition of subsequent nucleotide units, with each addition involving a number of chemical reactions.

The two primary methods of oligonucleotide synthesis, which are well-established in the art, are the so-called "phosphotriester" and "phosphoramidite" methods (described at some length in the references cited below). In the most prevalent schemes for both methods, the oligonucleotide chain grows by nucleophilic attack of the 5'-OH of the immobilized oligomer on an activated 3'-phosphate or phosphoramidite function of a soluble 5'-protected nucleotide building block. Other key steps include the acid deprotection of the 5'-O-(4,4'-dimethoxytrityl) group (DMT) in the phosphotriester method, and, in the phosphoramidite process, the oxidation of the phosphite triester to the phosphate triester.

Other methods of oligonucleotide synthesis are also known, including 5'-to-3' syntheses which use a $\beta$-cyanoethyl phosphate protecting group (De Napoli et al., Gazz. Chim. Ital. 114:65 (1984); Rosenthal et al., Tetrahedron Lett. 24:1691 (1983); Belagaje and Brush, Nucleic Acids Res. 10:6295 (1977); Cramer and Koster, Angew. Chem. Int. Ed. Engl. 7:473 (1968); and Blackburn et al., *J. Chem. Soc. C*, 2438 (1967)).

All of these methods of synthesizing oligonucleotides involve the use of 3'- and 5'-hydroxyl-protecting groups. Many of the hydroxyl-protecting groups used in oligonucleotide synthesis present some problems. For example, it is obviously desirable that a hydroxyl-protecting group be "orthogonal, " i e. . , removable with reagents that do not affect the remainder of the molecule, including other blocking or protecting groups which may be present. Some of the known hydroxyl-protecting groups are not completely "orthogonal". Also, many of the currently used hydroxyl-protecting groups, e.g., the levulinyl group, require removal with harsh reagents (e.g., acid in the case of dimethoxytrityl). The need for harsh reagents can damage a growing oligonucleotide chain and, furthermore, severely limits the number and type of protecting groups which may be employed elsewhere in the molecule during synthesis. Finally, it is desirable that the hydroxyl-protecting group be chemically stable in relation to whatever reagents are to be used in the chemical reactions involving the remainder of the molecule. It has proved difficult to find hydroxyl-protecting groups which are chemically stable as "bound" during use yet which are readily removable with relatively mild reagents. The invention is directed to orthogonal hydroxyl-protecting groups which are in fact quite stable while bound to the protected molecule, but which are nevertheless easily removable post-reaction with mild reagents. The present invention makes use of protecting groups which, when bound to the protected molecule, are in an oxidized, stable state, but which upon reduction become labile and are thus readily removable. The novel hydroxyl-protecting groups may also be used when there is more than one hydroxyl group present in the molecule to be protected. These protecting groups have been found by the inventors herein to be extremely versatile and invaluable as hydroxyl-protecting groups in general and more particularly in the chemical synthesis of oligonucleotides.

DESCRIPTION OF THE RELEVANT LITERATURE

In addition to the references cited and discussed in the preceding section, the following references also relate to one or more aspects of the present invention.

D. S. Kemp et al., *Tetrahedron Letters*, No. 12, pp. 1031–1034 (1977), describe the use of Maq esters as carboxyl protecting groups, specifically for use in the chemical synthesis of peptides.

N. Balgobin et al., *Chemica Scripta* 20:198–200 (1982), describe the use of 2-oxymethyleneanthraquinone as a terminal phosphate protecting group in the chemical synthesis of DNA and RNA.

R. L. Blankespoor et al., *J. Org. Chem*,. 49:4441–46 (1984), describe the use of the 2-methylene-9,10anthraquinone (Maq) ester to bind a $\gamma$-aminobutyric acid. The focus is on the development of an improved delivery system for neurotransmitters (i.e., such as 7-aminobutyric acid (GABA)). The authors note that the Maq ester is cleavable upon electroreduction to give the corresponding hydroquinone.

SUMMARY OF THE INVENTION

Accordingly, it is a primary object of the invention to provide methods and reagents for protecting hydroxyl groups, particularly during the chemical synthesis of oligonucleotides.

It is another object of the invention to provide orthogonally removable hydroxyl-protecting groups which are rendered labile and removable upon reduction with a liquid reducing agent.

It is still another object of the invention to provide a multifunctional nucleic acid derivatized at the N4-position with an oxyalkylene moiety -$(CH_2)_x$-OR where R is a hydroxyl-protecting group as will be described in detail herein.

It is yet another object of the invention to provide oligonucleotide chains containing such multifunctional nucleic acids.

It is a further object of the invention to provide a method of protecting a hydroxyl group of a hydroxyl-containing compound during chemical reaction of other functional groups contained within the compound which involves, prior to such chemical reaction, reacting the hydroxyl group to be protected with a chloroformate derivative of the desired protecting species.

It is still a further object of the invention to provide an improved method for chemically synthesizing oligonucleotides from nucleotide monomers. The improvement is directed to the use of certain orthogonally removable hydroxyl-protecting groups as will be described herein.

It is yet a further object of the invention to provide a method of making a branched oligonucleotide structure, which involves derivatizing a linear oligonucleotide at the N4-position of cytosine residues with secondary oligonucleotide chains, using the orthogonally removable hydroxyl-protecting groups of the invention at the N4 "branch points" during synthesis.

Additional objects, advantages and novel features of the invention will be set forth in part in the description which follows, and in part will become apparent to those skilled in the art on examination of the following, or may be learned by practice of the invention.

In one aspect of the invention, a method for protecting a hydroxyl group of a hydroxyl-containing compound during chemical reaction of other functional groups contained within the compound is provided. The method involves reaction with a protecting species to give rise to a protected or "blocked" hydroxyl group -OR, wherein R is in a stable oxidized form as bound, but which is readily removable upon reduction with a liquid reducing agent.

In other aspects of the invention, methods for synthesizing linear and branched oligonucleotides are provided which make use of orthogonally removable hydroxyl-protecting groups that are rendered labile and thus readily removable upon reduction.

In still other aspects of the invention, multifunctional nucleic acids containing orthogonally removable hydroxyl-protecting groups bound to the N4-position of cytosine through an oxyalkylene linkage are provided. Such multifunctional nucleic acids are useful in the synthesis of branched oligonucleotide structures by virtue of the orthogonally removable group at the N4-position. Oligonucleotide chains containing such multifunctional nucleic acids are provided as well.

DETAILED DESCRIPTION OF THE INVENTION

1. Definitions:

As used herein the terms "oligonucleotide" and "polynucleotide" shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine base, or of a modified purine or pyrimidine base, The term "nucleoside" will similarly be generic to ribonucleosides, deoxyribonucleosides, or to any other nucleoside which is an N-glycoside of a purine or pyrimidine base, or of a modified purine or pyrimidine base. There is no intended distinction in length between the term "oligonucleotide" and "polynucleotide" and these terms will be used interchangeably. These oligonucleotides and polynucleotides may be single-stranded or double-stranded, typically single-stranded. Also, the oligonucleotides of the present invention are normally of from about 2 to about 2000 monomer units; and more typically, for most probe-based applications, from about 2 to about 100 monomer units.

"Derivatizable" nucleotides as used herein are nucleotides modified so as to include at the 4-position of a pyrimidine, e.g., cytosine, a functional group which can react with the protecting species described herein in which, furthermore, can be used to initiate synthesis of secondary oligonucleotide chains in the preparation of branched oligonucleotide structures. An example of a derivatizable nucleotide is one which has been modified at the 4-position with an oxyalkylene moiety so that a free hydroxyl group is present at that position of the molecule.

A hydroxyl group that is "protected" is one that has been reacted with a protecting moiety such that the resulting protected group will not be susceptible to any undesired chemical reaction during the synthetic step or steps during which the protecting group is present.

By "stability" of the hydroxyl-protected compound or of the hydroxyl-protecting group when covalently bound to the hydroxyl-containing compound, is meant substantial absence of steric interference as well as inherent chemical stability, i.e., resistance to attack and/or degradation.

By "lower alkyl" and "lower alkoxy" are meant alkyl and alkoxy substituents, respectively, having from about 1 to 8, more typically from about 1 to 6, carbon atoms.

Where aromatic substituents are indicated, it is to be understood that each individual aromatic ring may be substituted at one or more carbon atoms with moieties which do not adversely affect function or reactivity.

2. Hydroxyl Group Protection:

The method of the invention is thus useful for protecting a free hydroxyl group of a hydroxyl-containing compound so as to preserve the hydroxyl functionality during chemical reaction or chemical conversion of other functionalities present on the molecule. In general terms, the hydroxyl group to be protected is reacted with a protecting species to give rise to a moiety -OR. In a preferred embodiment, R is Maq or a derivative thereof. In such a case, R may be represented by the structural formula

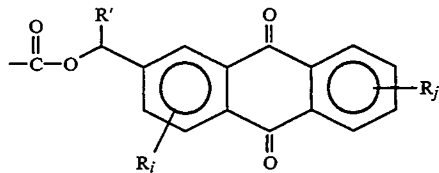

in which R' is hydrogen, aryl, or aralkyl, the $R_i$ may be the same or different and are selected from the group consisting of amino, nitro, halogeno, hydroxyl, lower alkyl and lower alkoxy; the $R_j$ may be the same or different and are selected from the group consisting of amino, nitro, halogeno, hydroxyl, lower alkyl and lower alkoxy; i is. zero, 1, 2 or 3; and j is zero, 1, 2, 3 or 4.

In this structure, R' is preferably hydrogen or phenyl. The $R_i$ and $R_j$, as indicated, may represent any one of a number of different substituents. The substituents can be selected to render the protecting moiety more easily reduced and thus more readily removed from the protected hydroxyl functionality. Alternatively, substituents may be selected which render the group more difficult to remove and thus more stable when bound. Substitution at the 1, 4, 5 and/or 8 positions will give rise to the greatest effect.

In an alternative embodiment, R is

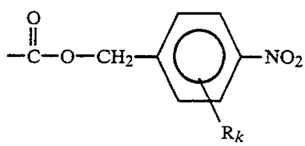

in which k is zero, 1, 2, 3 or 4; and the $R_k$ may be the same or different and are selected from the group consisting of amino, nitro, halogeno, hydroxyl, lower alkyl and lower alkoxy. A preferred example of such a species is p-nitrobenzyl.

The free hydroxyl group to be protected is derivatized with a protecting species as just described preferably by reaction with the chloroformate derivative. That is, to provide a protecting group which is Maq or a Maq derivative, reaction would be carried out between the hydroxyl-containing compound and the chloroformate

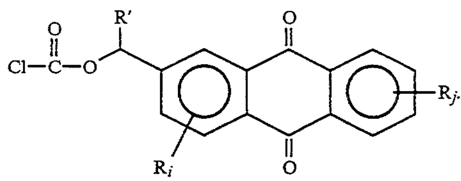

Where R is p-nitrobenzyl or a derivative thereof, again, reaction would preferably be carried out with the chloroformate

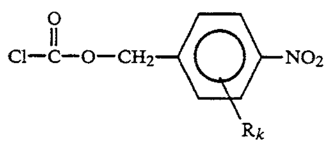

Reaction is preferably carried out in an anhydrous solvent at a relatively low temperature, i.e., lower than about 20° C., more preferably at or below about 0° C. The chloroformate derivatives themselves may be readily synthesized from the hydroxymethyl analog with triphosgen.

Although these reducible hydroxyl-protecting groups may be used in conjunction with a wide variety of molecular structures and synthetic steps, they have been found to be particularly useful in the chemical synthesis of oligonucleotides, including short oligonucleotide chains useful for probe-type applications as well as longer and/or more complex, e.g., branched oligonucleotide structures. The inventors herein have found these reducible hydroxyl-protecting groups to be an excellent alternative to the dimethoxytrityl (DMT) and pixyl groups at the 5'-hydroxyl position. Use at the 3'-hydroxyl of either a nucleotide or an oligonucleotide chain is also possible.

A further application of the hydroxyl-protecting groups of the invention, as will be described in more detail below, is in the blocking of an exocyclic hydroxyl group present at the N4-position of a 5-methyl cytosine residue. A protecting group is necessary in such a structure when the N4-position of cytosine residues, i.e., contained within an oligonucleotide chain, are used as branch points for the synthesis of secondary oligonucleotide chains orthogonal to the backbone of the starting material.

While several of the references cited and discussed hereinabove disclose the use of reducible protecting groups for phosphate or carboxyl moieties, the use of such structures for the protection of hydroxyl species is new and provides a number of important and distinct advantages. First of all, relatively mild reagents can be used to reduce the bound protecting group and thus render it labile and removable. In the case of Maq, for example, dithionite may be used. This is in contrast to the need for a reagent such as acid, which is required when the dimethoxytrityl group is used for hydroxyl protection. The ability to use mild reagents minimizes the likelihood of damage to the oligonucleotide structure being synthesized. These reducible protecting groups are also orthogonal in that they are quite specific and not chemically vulnerable to most chemical reagents unless reduced. Again, these reducible protecting groups work by binding to the hydroxyl group to be protected in an oxidized, chemically very stable state, but are rendered labile when reduced. With the Maq ester for example, cleavage at the ester site is expected to be rapid for the hydroquinone form (see, e.g., D. S. Kemp et al., cited above), while in the quinone form, resistance to cleavage would be expected. Finally, one additional and critically important advantage should be noted. This is that use of these hydroxyl protecting groups in DNA synthesis substantially reduces the likelihood of depurination when acid-labile protection is employed, and thus eliminates the corresponding large loss in yield. This is an important advantage for all of the DNA synthesis applications discussed herein as well as others which might be envisioned by those skilled in the art upon reading the present disclosure.

3. Chemical Synthesis of Oligonucleotides Using Orthogonally Removable Hydroxyl-Protecting Groups:

As noted above, an important application of the present hydroxyl-protecting groups and methods is in the chemical synthesis of both linear and branched oligonucleotides. As is now well-known in the art, methods for synthesizing oligonucleotides typically involve sequential addition of 3'-blocked and 5'-blocked nucleotide monomers to the terminal 5'-hydroxyl group of a growing oligonucleotide chain, where each addition is effected by nucleophilic attack of the terminal 5'-hydroxyl group of the growing chain on the 3'-position of the added monomer, which is typically a phosphorus derivative such as a phosphotriester, phosphoramidite, or the like. Such procedures are described in detail in the references cited and discussed in the "Background" section herein.

Another aspect of the invention thus involves use of orthogonally removable, reducible hydroxyl-protecting groups as either said 3'- or 5'-blocking groups or both. The use of the reducible protecting groups is preferred at the 5'-position as an alternative to the well-known protecting moieties dimethoxytrityl and pixyl.

The hydroxyl-protecting groups of the invention are additionally useful in the formation of branched oligonucleotide structures, e.g., nucleic acid multimers useful in "amplified" nucleic acid hybridization assays, as described in copending, commonly assigned U.S. patent application Ser. No. 340,031, filed Apr. 18, 1989,now U.S. Pat. No. 5,124,246 and incorporated herein by reference. As described in that application, the N4-position of cytosine residues within an oligonucleotide chain is modified so as to contain an oxyalkylene moiety which may then be derivatized to give rise to secondary oligonucleotide chains in a branched structure. In the aforementioned patent application, such branched structures are termed "nucleic acid multimers". These multimers are useful in nucleic acid hybridization assays as follows. The multimers are bound to the analyte nucleic acid or to a single-stranded oligonucleotide bound to the analyte. Since the multimer includes a relatively large number of oligonucleotide units that are available for binding with the labeled oligonucleotide, many more label groups may be bound to the analyte than in prior procedures. The large number of label groups decreases the threshold level of detectable analyte, in some instances to the subattomole (10–18 mole level).

The multimers may be used in essentially any of the known nucleic acid hybridization formats, such as those in which the analyte is bound directly to a solid phase or sandwich hybridizations in which the analyte is bound to an oligonucleotide that is in turn bound to a solid phase.

The hybridization reaction is usually done in an aqueous medium, particularly a buffered aqueous medium, which may include various additives. Additives which may be employed include low concentrations of detergent (0.1 to 1%), salts, e.g., sodium citrate (0.017 to 0.170 M), Ficoll, polyvinylpyrrolidine, carrier nucleic acids, carrier proteins, etc. Nonaqueous solvents may be added to the aqueous medium, such as dimethylformamide, dimethylsulfoxide, alcohols, and formamide. These other solvents will be present in amounts ranging from 2 to 50%.

The stringency of the hybridization medium may be controlled by temperature, salt concentration, solvent system, and the like. Thus, depending upon the length and nature of the sequence of interest, the stringency will be varied.

Various techniques can be employed for detecting the presence of the label groups. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques available to immunoassays can be employed with the subject assays.

The multimers may be used in hybridization assays in which the analyte nucleic acid is bound directly to a solid phase, such as a "dot blot" assay, or in other assays such as direct, indirect, and sandwich immunoassays. The referenced application describes the use of the levulinyl group as the hydroxyl-protecting moiety at the N4-position (the levulinyl group requires removal with hydrazine or a similar reagent, which can give rise to destabilization).

In the present method, the branched oligonucleotide structure is made by first providing an oligonucleotide chain the cytosine residues of which have been N4-derivatized to give -$(CH_2)_x$-OR moieties wherein R is as defined above, capping the 3'- and 5'-terminal hydroxyl groups of the chain, removing the hydroxyl-protecting groups R by treatment with a liquid reducing agent, thereby giving rise to free hydroxyl groups bound through an alkylene linking group to the N4-position, and finally synthesizing secondary oligonucleotide chains at the free hydroxyl groups which then serve as the branch points.

4. Multifunctional Nucleic Acids and Oligonucleotides Containing the Same:

In another embodiment, the present invention encompasses multifunctional nucleic acids derivatized so as to contain the moiety -$(CH_2)_x$-OR at the N4-position, wherein R is as defined above, as well as oligonucleotides containing such derivatized multifunctional nucleic acids. The multifunctional nucleic acids have the structure

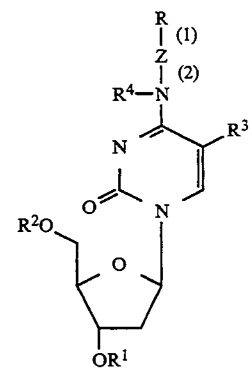

wherein R is a hydroxyl protecting group that can be removed and replaced, without affecting $R^1$ or $R^2$ by reduction with a liquid reducing agent; $R^1$ is a phosphorus derivative that enables addition of nucleotides to the 5'-position of an oligonucleotide chain during chemical synthesis; $R^2$ is a protecting group that is generally base-stable and acid-sensitive; $R^3$ is selected from the group consisting of hydrogen, methyl, I, Br and F; $R^4$ is hydrogen or methyl; and Z is selected from the group consisting of

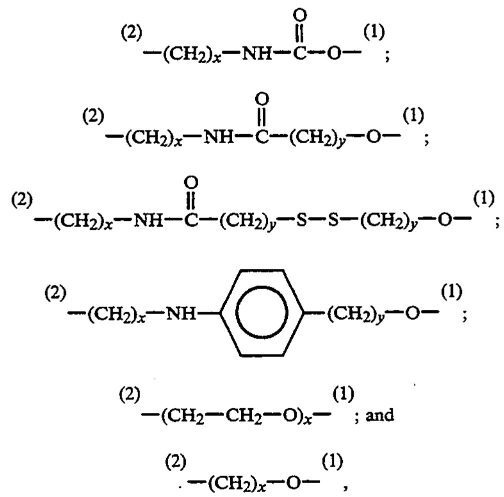

wherein x and y may be the same or different and are integers in the range of 1 to 8 inclusive. (The designations "(1)" and "(2)" at the Z linkage indicate the orientation of the Z linker moiety.)

In this structure, it is preferred that Z be -$(CH_2)$x-, $R^1$ be a phosphoramidite, a phosphodiester or a phosphotriester, while it is similarly preferred that $R^2$ be dimethoxytrityl or pixyl. R, as described throughout the present application, is an orthogonally removable hydroxyl-protecting group reducible with a liquid reducing agent to give rise to a labile, easily removable species.

Oligonucleotide chains containing these modified cytosine residues, i.e., derivatized modified nucleotides as just described, thus have the structure

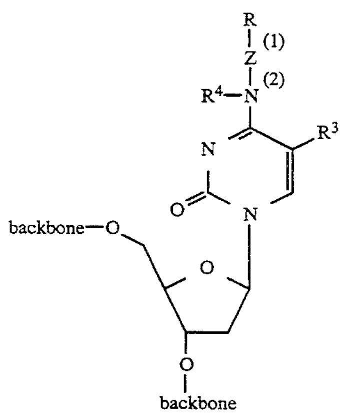

R, $R^3$, $R^4$, Z, x and y are as defined above.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Example 1

Use of Carbonate Esters of 2-(hydroxymethyl)anthraquinone (MAC Derived from Methoxyanthraquinone oxycarbonyl) to Protect E. Exocyclic Alkyl Hydroxyl Group in Branching Monomers The MAQ moiety (methoxyanthraquinone) has been utilized to protect: a) carboxylic acids as MAQ esters (MAC; D.S. Kemp and J. Reczek, Tetrahedron letters 12, p 1031–1034 (1977)), b) amines as a MAQ urethane (R. L. Blankespoor, A. N. K. Law and L. L. Miller, *Journal of Organic Chemistry* 49, p 4441–4446 (1984)), and c) phosphate diesters as the MAQ phosphotriester (N. Balgobin, M. Kwaitkowski and J. Chattopadhyaya, Chemica Scripta 20, p 198–200 (1982)).

Deprotection of the MAC carbonate esters is effected by treatment with sodium dithionite under neutral conditions. The MAC group is orthogonal to other protecting groups (PG) used in DNA chemical synthesis, i.e., it can be removed under conditions that do not destabilize other protecting groups used (see table), nor does the sodium dithionite solution damage the native DNA bases. The use of MAC for hydroxyl group protection has not been reported. The mild conditions for its removal may make it useful in protection of 5'-hydroxy groups in DNA and RNA synthesis.

2-(Hydroxymethyl)anthraquinone is converted to the corresponding chloroformate (MAC-Cl) with triphosgen. The MAC-Cl reacts specifically with the primary hydroxy group of N-4-(6-hydroxyhexyl)-5'-DMT-5-methyl-2'-deoxycytidine.

The synthesis conditions for making large quantities (25 millimole scale) have been worked out, and the synthesis of branched DNA molecules has been conducted.

TABLE 1

Stability of Selected Protecting Groups
Yields are reported in %, where 100% indicates no deprotection and/or modification as judged by TLC analysis after 1 and 18 hours. The sodium dithionite solution was prepared by dissolving 1 gram of solid sodium dithionite in 20 ml of 1 M triethyl-ammonium bicarbonate, followed by addition of 20 ml dioxane.

| Functionality in DNA | 1 hour | 18 hours |
|---|---|---|
| succinate | 100 | 100 |
| A (benzyl) | 100 | >95 |
| C (benzyl) | 100 | >90 |
| G (isobutyl) | 100 | 100 |
| T | 100 | 100 |
| BM2 (deprotected MAC) | 100 | 100 |
| BM2 (levulinyl) | 100 | 100 |
| P-O-cyanoethyl | >85 | <5 |
| P-O-methyl | 100 | >95 |

Preparation of 2-anthraquinonemethoxy chloroformate (MAC-Cl):

A 0.1 molar solution of 2-(hydroxymethyl)-anthraquinone (MAQ-OH) was prepared by dissolving 25 mmole (5.95 g) in 250 ml dioxane. The yellow solution was filtered and the solvent removed by evaporation to remove water. The residue was redissolved in 200 ml dioxane and pyridine (2 ml; 25 mmole) was added. This solution was added dropwise to a stirred solution of triphosgen (2.5 g; 25 Meq) in 50 ml $CH_2Cl_2$ at 0° C. After ended addition the mixture was stirred at 20° C for 18 hours. The mixture was diluted with 800 ml ethyl acetate and the organic phase washed with 3×600 ml 80% saturated aqueous NaCl solution. After drying of the organic phase over $NaSO_4$ the solvent was removed in vacuo to give a yellow solid, which was dissolved in $CH_2CL_2$ (250 ml; 0.1 M). This solution was used without further purification.

Preparation of 5'-DMT-N-4-(O-2-anthraquinone-methoxycarbonyl-6-oxyhexyl)-5-methyl-2'-deoxycytidine 3'-P-N,N-diisopropylmethylphosphoramidite ("E Base" or "E"):

To a solution of N-4-(6-hydroxyhexyl)-5'-DMT-5-methyl-2'deoxycytidine (17 mmole), prepared as previously described (Horn and Urdea, NAR vol. 17:17, p. 6959–6967 (1989)), in 200 ml methylene chloride was added pyridine (40 mmole) and the mixture was cooled to 0° C. A solution of MAC-Cl (20 mmole) in 200 ml of $CH_2Cl_2$ was added dropwise and left stirring for 10 minutes. TLC analysis (silica plates developed with 10% methanol/$CH_2CL_2$) showed that the starting material had been completely consumed. The reaction mixture was diluted with 400 ml ethyl acetate and the organic phase extracted with 2×300 ml 5% $NaHCO_3$ and 80% saturated aqueous NaCl. After drying of the organic phase over $Na_2SO_4$ for 30 minutes followed by filtration the solvent was removed in vacuo. The product was purified by silica gel Chromatography using a gradient of methanol (0–6%) in $CH_2Cl_2$ to give 13 g of pure product (85% yield).

The nucleoside N-4-(0-anthraquinone-methoxycarbonyl-6-oxyhexyl)-5'-DMT-5-methyl-2'-deoxycytidine (14.4 mmole) was dissolved in $CH_2Cl_2$ (50 ml) containing 70 mmole DIPEA. After cooling to 0° C. N,N-diisopropylaminomethoxychlorophosphine was added (2.72 ml; 14 mmole). The phosphitylating agent was added in small portions until 95% of the starting material had been consumed. The reaction mixture was then diluted with ethyl acetate (300 ml), extracted with 2×300 ml 5% $NaHCO_3$ then 2×300 ml 80% saturated aqueous NaCl and finally dried over solid $Na_2SO_4$. The solvent was removed in vacuo.

The crude phosphoramidite was purified by silica gel chromatography using the solvent system methylene chloride/ethyl acetate/triethylamine (49:49:2 v/v), and the fractions containing the product were pooled and concentrated. After coevaporation with toluene, the purified phosphoramidite was dissolved in toluene and added with rapid stirring to 800 ml of cold hexanes (−50° C.). the resulting precipitate was rapidly collected by filtration and dried in high vacuum for 18 hours to give 12.4 g of a slightly yellow solid (81% yield). NMR $^{31}p$: 8 145 ppm.

A DNA oligomer was synthesized on a 3000 A CPG support (40 mg) with the sequence 3′-TCC-GTA-TCC-TGG-GCA-CAG-TTE $(MAC)_{15}$ using the standard 1 micromole scale program using methyl phosphoramidite on the ABI 380B. The support was next treated with a solution of 1 g $Na_2S_2O_4$ in 20 ml 1M TEAB/10 ml dioxane for 30 minutes to remove the MAC group. After filtration and washing with water and $CH_3CN$ the solid support was dried. The secondary synthesis to introduce the secondary sequence "X" was performed on ABI 380B using a special double condensation cycle to incorporate 15 identical copies of the sequence 3′-GTC-AGT-5′ ("X"). During synthesis DMT removal was achieved with 3% DCA in toluene/3% TCA in $CH_2Cl_2$ (1:1 v/v) using high flow rate. Complete deprotection of the 15 secondary site branched DNA was achieved with 3% DCA in toluene to remove DMT groups and thiophenol/TEA/dioxane to remove methyl groups from phosphotriesters on the solid-supported fragment. The fragment was released with $NH_4OH$ at 20° C. for 1 hour and exocyclic N-protecting groups were removed with hot $NH_4OH$ at 60° C. for 18 hours. After removal of the volatile solvent, the product was analyzed by PAGE.

By analogy, when N-4-(O-levulinyl-6-oxyhexyl)-5-methyl-2′-deoxycytidine is used the lev group was removed with a solution of 0.5 M hydrazine hydrate in pyridine/acetic acid (4:1 v/v) for 90 minutes prior to secondary synthesis.

We claim:

1. A compound of the formula

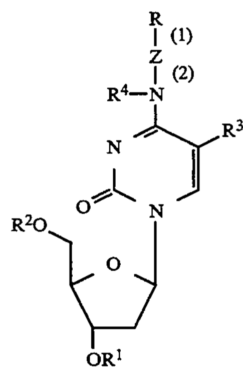

wherein:

R is selected from the group consisting of

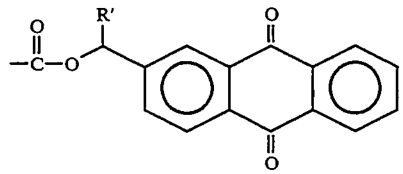

and

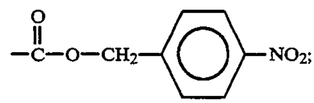

R′ is hydrogen or phenyl;

$R^1$ is a phosphorus derivative that enables addition of nucleotides to the 5′-position of an oligonucleotide chain during chemical synthesis, and is a phosphoramidite, a phosphodiester or a phosphotriester;

$R^2$ is an acid-sensitive, base-stable protecting group;

$R^3$ is selected from the group consisting of hydrogen, methyl, I, Br and F;

$R^4$ is hydrogen or methyl; and

Z is selected from the group consisting of

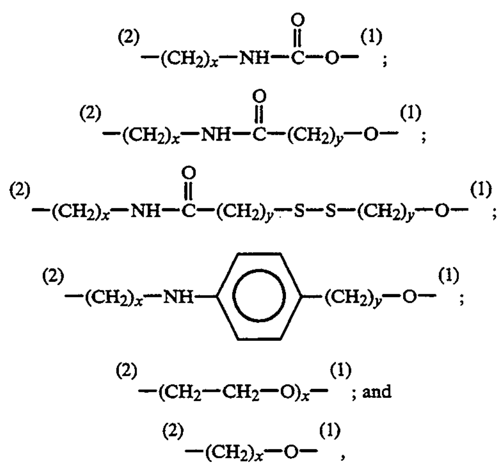

wherein x and y may be the same or different and are integers in the range of 1 to 8 inclusive.

2. The compound of claim 1 wherein $R^2$ is dimethoxytrityl or pixyl.

3. The compound of claim 1 wherein R has the structure

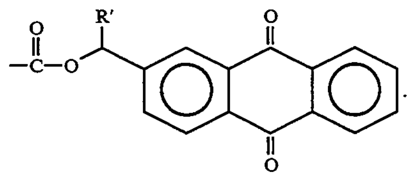

4. The compound of claim 3 wherein R′ is hydrogen.

5. The compound of claims 3 wherein R′ is phenyl.

6. The compound of claim 2 wherein R is 2-oxymethyleneanthraquinone.

7. The compound of claim 1 wherein R is

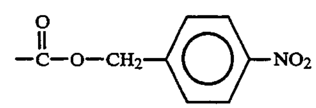

* * * * *